(12) United States Patent  
Sommer et al.

(10) Patent No.: US 8,268,161 B2
(45) Date of Patent: *Sep. 18, 2012

(54) ELECTROCHEMICAL SENSOR HAVING A MEDIATOR COMPOUND WITH A SOLID

(75) Inventors: Sabrina Sommer, Luebeck (DE); Herbert Kiesele, Luebeck (DE); Frank Mett, Luebeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 1607 days.

This patent is subject to a terminal disclaimer.

(21) Appl. No.: 11/677,782

(22) Filed: Feb. 22, 2007

(65) Prior Publication Data

US 2008/0035493 A1    Feb. 14, 2008

(30) Foreign Application Priority Data

Mar. 30, 2006    (DE) .......................... 10 2006 014 715

(51) Int. Cl.
*G01N 27/413*    (2006.01)

(52) U.S. Cl. ...................... 205/786.5; 204/431; 205/793

(58) Field of Classification Search .................. 204/400, 204/403.06, 431; 205/793, 794.5, 786.5
See application file for complete search history.

(56) References Cited

U.S. PATENT DOCUMENTS

| | | | |
|---|---|---|---|
| 3,795,589 A | 3/1974 | Dahms | |
| 4,522,690 A * | 6/1985 | Venkatasetty | 205/783 |
| 4,894,138 A | 1/1990 | Gambert et al. | |
| 5,521,101 A * | 5/1996 | Saini et al. | 205/777.5 |
| 6,231,815 B1 * | 5/2001 | Bainczyk et al. | 422/102 |
| 6,461,496 B1 * | 10/2002 | Feldman et al. | 205/777.5 |
| 6,605,201 B1 * | 8/2003 | Mao et al. | 204/403.14 |
| 6,607,642 B1 * | 8/2003 | Kiesele et al. | 204/415 |
| 7,005,048 B1 * | 2/2006 | Watanabe et al. | 204/403.14 |
| 7,615,139 B2 * | 11/2009 | Kiesele et al. | 204/412 |
| 2002/0005352 A1 | 1/2002 | Offenbacher | |
| 2002/0070112 A1 * | 6/2002 | Lee et al. | 204/431 |
| 2004/0074780 A1 * | 4/2004 | Twardowski et al. | 205/618 |
| 2006/0021881 A1 | 2/2006 | Soundarrajan et al. | |
| 2006/0237313 A1 * | 10/2006 | Kiesele et al. | 204/412 |
| 2007/0227910 A1 * | 10/2007 | Sommer et al. | 205/786.5 |

FOREIGN PATENT DOCUMENTS

| | | |
|---|---|---|
| DE | 199 39 011 C1 | 1/2001 |
| DE | 101 44 862 A1 | 3/2003 |
| EP | 0887641 A1 * | 12/1998 |
| FR | 2764985 A | 12/1998 |
| FR | 2781284 A | 1/2000 |
| GB | 2326485 A | 12/1998 |
| GB | 2330414 A | 4/1999 |
| GB | 2353363 A | 2/2001 |

OTHER PUBLICATIONS

Merriam-Webster Online Dictionary defintion of excess.*

* cited by examiner

*Primary Examiner* — Kaj K Olsen
*Assistant Examiner* — Susan D Leong
(74) *Attorney, Agent, or Firm* — McGlew and Tuttle, P.C.

(57) ABSTRACT

An electrochemical sensor is provided especially for gases. The electrochemical sensor has a mediator compound, which is both dissolved in an electrolyte (9) in a saturated form and is present as an excess solid (10) in the electrolyte (9).

21 Claims, 2 Drawing Sheets

ELECTROCHEMICAL SENSOR HAVING A MEDIATOR COMPOUND WITH A SOLID

CROSS REFERENCE TO RELATED APPLICATIONS

This application claims the benefit of priority under 35 U.S.C. §119 of German Patent Application DE 10 2006 014 715.4 filed Mar. 30, 2006, the entire contents of which are incorporated herein by reference.

FIELD OF THE INVENTION

The present invention pertains to an electrochemical sensor, especially for gases, having a mediator compound.

BACKGROUND OF THE INVENTION

Electrochemical measuring cells are widely used in the analysis of substances, for which potentiometry, voltammetry/polarography, coulometry and conductometry can be mentioned as the most important principles of measurement. The use of electrochemical measuring cells for the analysis of gases has been known for a long time as well. However, there are efforts to develop new, more sensitive and more reliable sensors, especially when toxic gases in the parts per billion (ppb) range are to be detected and possibly even quantitatively determined.

For the purpose of highly sensitive analysis, such electrochemical gas detectors are required to meet the following requirements:

low residual current $I_0$;
no or at most only very slight effect of variations in the humidity of the air and/or the air temperature on the residual current $I_0$;
low cross sensitivity to interfering gases;
low double-layer capacity of the measuring electrode, especially in relation to dynamic measurement methods; and
high long-term stability.

The properties of an electrochemical gas sensor are determined decisively by the material, the morphology and the layer thickness of the measuring electrode.

Platinum, gold or graphite are mentioned as the measuring electrode materials in, e.g., U.S. Pat. No. 3,795,589. Very many gases can be reacted directly, i.e., without a mediator, on the catalytically highly active precious metals platinum and gold. Therefore, it is often impossible to reach the desired selectivity. The long-term stability of the catalytically less active graphite electrodes is low and these electrodes show, depending on the electrode potential, a high cross sensitivity to NO and $NO_2$.

DE 199 39 011 C1 discloses a sensor, whose measuring electrode consists of diamond-like carbon (DLC). DE 101 44 862 A1 pertains to a measuring electrode consisting of boron-doped diamond (BDD). These electrode materials usually require mediators, because most gases cannot be directly reacted on these electrodes.

SUMMARY OF THE INVENTION

The object of the present invention is to provide a gas sensor with reduced cross sensitivity to interfering gases, short response time and high sensitivity to the analyte gas.

According to the present invention, an electrochemical gas sensor is provided for detecting an analyte. The electrochemical gas sensor includes a housing defining an electrolyte space as well as a measuring electrode comprising a carbon-containing material. The measuring electrode is disposed in the electrolyte space. An auxiliary electrode is disposed in the electrolyte space. A liquid electrolyte is disposed in the electrolyte space. The electrolyte solution is saturated with a mediator, the mediator additionally being contained as a solid in the electrolyte.

The quantity of solid is advantageously selected according to the present invention such that a sufficient quantity of solid mediator substance is still present even at the highest allowable temperatures, mostly +60° C.

The preparation may be carried out by introducing the electrolyte containing the mediator into the sensor as a hot, saturated solution. As an alternative, a precipitate can be formed in the sensor due to a plurality of solutions being poured together. Furthermore, it is possible to fill the electrolyte and the mediator into the sensor in the form of a suspension.

A gas sensor with the mediator suspension according to the present invention has the advantage that a solution saturated with mediator is present for all ambient conditions. The signal characteristic is therefore nearly independent from the relative humidity of the air. Since hardly any concentration gradients develop in the electrolyte, the sensor is not sensitive to shaking.

A mediator that contains transition metal salts of polybasic acids and/or transition metal salts of polyhydroxycarboxylic acids can be used especially advantageously.

These mediator compounds are specifically compounds that contain at least one additional group selected from among hydroxyl and acid groups, besides at least one acid group. In particular, the mediator compound is a carboxylic acid salt having, besides the one carboxylic acid group, at least one hydroxyl group, preferably at least two hydroxyl groups and/or at least one additional carboxylic acid group. Tetraborates, such as sodium tetraborate or lithium tetraborate, are also suitable compounds.

Transition metal salts, especially Cu salts of such mediators, permit the selective determination of $SO_2$. However, such mediator compounds can also be used to determine the concentrations of other target gases, e.g., $H_2S$.

It was surprisingly found that the $Fe^{3+}$ salts, such as iron hydrogen phthalate or iron phthalate, are especially suitable for use for the determination of $H_2S$ among the mediator compounds according to the present invention. Formation of elemental sulfur was not observed. Contrary to commercially available sensors, such sensors also do not show cross sensitivity to $SO_2$.

The mediators according to the present invention have, furthermore, pH buffering properties, so that the sensors can be exposed to the gas over several hours without loss of sensitivity.

The mediators are preferably poorly soluble in the liquid gas sensor composition. The use of suspensions or solutions of the mediator with excess solid offers a number of other advantages, such as:

Constant mediator concentration with variable air humidity;
identical equilibrium potentials at the measuring electrode and the reference electrode,
filter action of the excess solid; and
the sensor can be operated under anaerobic conditions if the reference electrode also consists of carbon and the mediator determines the potential of that electrode.

Preferably hygroscopic alkali or alkaline earth metal halides, preferably chlorides, are used as conductive electrolytes in aqueous solution. If organic solvents, e.g., ethylene carbonate and/or propylene carbonate, are used, it is also possible to use, e.g., ammonium halides.

Preferred are measuring electrodes from diamond-like carbon (DLC), especially those known from DE 101 44 862 A1, or measuring electrodes from boron-doped diamond (BDD), whose electrode material makes possible an even larger potential window than DLC electrodes and can also be used in case of extreme requirements, e.g., when determining an analyte with extremely high oxidation potential or very low reduction potential. DLC, which can be manufactured in a simple manner and at low cost, is sufficient for many analytes.

The disclosure of DE 199 39 011 C1 and corresponding U.S. Pat. No. 6,607,642, in which measuring electrodes made of diamond-like carbon, and of DE 101 44 862 A1 and corresponding U.S. Pat. No. 6,584,827, in which a measuring electrode made of boron-doped diamond (BDD) is disclosed, are also made hereby expressly part of the disclosure of the present invention by reference (hereby incorporated by reference in their entirety) especially concerning the design of the gas sensor and especially concerning the measuring electrode.

It is suspected that the BDD and DLC electrode material in combination with redox-inactive electrolytes always requires an analyte that is capable of effecting an "outer sphere electron transfer" in contact with the electrode. Since only a small number of target gases accomplish such a charge transfer between the electrode and the target gas according to the experience currently available, it is necessary to add a mediator, which mediates a reaction on the measuring electrode, to the electrolyte solution.

The additional presence of a mediator offers the possibility of making available a sensor that is highly selective against the desired analyte gas by selecting suitable mediators.

In measuring electrodes made of DLC, diamond-like carbon is applied in a very thin layer to a gas-permeable membrane. The diamond-like carbon layer may be produced according to a radiofrequency magnetron sputtering method or by means of other coating methods as well. The thickness of the layer of diamond-like carbon is 50 nm to 1,000 nm.

In case of the design as a BDD electrode, the measuring electrode is applied as a thin layer of boron- or nitrogen-doped diamond to a porous substrate, the porous substrate preferably consisting of a nonwoven material consisting of chemically pure quartz. If the measuring electrode is formed on a porous carrier material, a separate gas-permeable membrane before the measuring electrode may be eliminated.

The thickness of the thin layer of doped diamond is 0.5 μm to 5 μm. In case of a layer consisting of boron-doped diamond, the doping consists of $10^{19}$ to $10^{21}$ boron atoms per cubic centimeter of diamond. For nitrogen, the doping is approximately $10^{20}$ nitrogen atoms per cubic centimeter of diamond.

Besides measuring electrodes consisting of DLC, BDD or precious metal (precious metal thin-layer electrode), so-called carbon nanotubes (CNT) are also suitable for use as a measuring electrode material. Carbon nanotubes are cylindrical carbon molecules from the family of the fullerenes, as they appear, for example, from EP 1 591 417 A1.

Measuring electrodes prepared from carbon nanotubes (CNT) have long-term stability, can be integrated in existing sensor constructions in a simple manner, are suitable for many mediators, and can be purchased at low cost. There are only a small number of cross sensitivities caused by the electrode material. This applies especially to multiwall carbon nanotubes (MW CNT). Such measuring electrodes are wetted by the electrolyte solution over their entire surface, as a result of which a large surface is obtained for the electrochemical reaction.

Carbon nanotubes have a structural relationship to the fullerenes, which can be prepared, e.g., by evaporating carbon according to a laser evaporation method. A single-wall carbon nanotube has, for example, a diameter of one nm and a length of about 1,000 nm. Besides single-wall carbon nanotubes, there are also double-wall carbon nanotubes (DW CNT) and structures with a plurality of walls (MW CNT).

Carbon nanotubes are provided, due to their production, with metal atoms, e.g., Fe, Ni, Co, including the oxides thereof, so that such carbon nanotubes possess catalytic activities on measuring electrodes. It proved to be advantageous to remove these metal particles by acid treatment.

However, it is possible to bind catalysts or mediators (e.g., porphyrins or phthalocyanines) specifically to the carbon nanotubes. However, it is generally preferable to add a soluble mediator to the electrolyte.

The carbon nanotubes are advantageously applied to a porous carrier, a nonwoven or a diffusion membrane. The carbon nanotubes are put together by self-aggregation or with a binder. Polytetrafluoroethylene (PTFE) powder is preferably used as the binder.

It is especially advantageous to prepare the carbon nanotubes from a prefabricated film, a so-called "buckypaper." The measuring electrode can then be punched out directly from the buckypaper. Large numbers can thus be produced at low cost.

The layer thickness of the carbon nanotubes on the measuring electrode depends on the structure of the measuring electrode.

If the carbon nanotubes are in the form of multiwall carbon nanotubes, the layer thickness is between one μm and 1,000 μm and preferably between 50 μm and 150 μm. The layer thickness is between 0.5 μm and 500 μm and preferably between 10 μm and 50 μm in the case of single-wall carbon nanotubes.

The layer thickness also depends on the purity of the material. The layer thickness is rather at the lower end of the range in case of especially pure material.

The layer thickness of precious metal thin-layer electrodes, which are usually prepared according to a sputtering process, is between 100 nm and 500 nm. The catalytic activity of precious metal thin-layer electrodes is much lower than that of the corresponding thick-layer electrodes, but higher than in DLC or BDD electrodes. The preferred layer thickness of precious metal thick-layer electrodes is between 200 μm and 500 μm.

Classical gas diffusion electrodes (thick layer) are less preferred, because they have a high residual current and low selectivities.

The measuring cell contains the measuring electrode and the auxiliary electrode as well as preferably also a protective electrode and a reference electrode. The sample contains the electrolyte solution and the redox mediator in the dissolved form and as an excess solid. The measuring cell has openings, which are provided with a membrane permeable to the analyte and otherwise close the measuring cell to the outside. The electrochemical cell contains a measuring electrode, protective electrode, reference electrode and the auxiliary electrode, which may be arranged in a coplanar, plane-parallel or radial arrangement in relation to one another and are flat. The gap between the plane-parallel electrodes may be filled with a separator, which is permeable to the liquid medium and spaces the electrodes apart.

The mode of operation of the measuring cell is as follows: When analyte gas is admitted to the membrane, whether the analyte gas is gaseous or dissolved in a medium, the analyte gas diffuses through the membrane into the electrolyte and is oxidized or reduced by the mediator. The transition metal reduced or oxidized in the process is re-oxidized or re-reduced at the measuring electrode.

The most important processes that take place in the area of the measuring electrode shall be briefly explained below on the basis of the example of $Cu^{2+}$ ions as a component of the mediator and of the analyte gas $SO_2$. The $SO_2$ diffusing into the measuring cell from the outside is first oxidized by $Cu^{2+}$, into $SO_4^{2-}$:

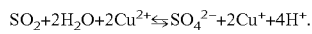
$$SO_2+2H_2O+2Cu^{2+} \leftrightarrows SO_4^{2-}+2Cu^++4H^+.$$

The resulting $Cu^+$ ions are re-oxidized at the measuring electrode:

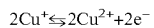
$$2Cu^+ \leftrightarrows 2Cu^{2+}+2e^-$$

The electrolyte-mediator mixture according to the present invention can be prepared as follows: So much $CuCl_2$ is added to an LiCl solution that a 0.2-1.0-molar and preferably 0.5-molar $CuCl_2$ will be formed.

The sensor has high sensitivity to $SO_2$ with this mediator. However, it has a cross sensitivity to $H_2S$ and elemental sulfur is formed, which leads to clogging of the membrane during prolonged exposure to the gas.

The resulting chloro complex can then be mixed, e.g., with potassium hydrogen phthalate, sodium tetraborate or trisodium citrate. The resulting concentration should preferably agree with the above $CuCl_2$ concentration and be especially about a 0.5-molar concentration.

A bluish-green precipitate is formed upon the addition of potassium hydrogen phthalate or sodium tetraborate. Copper hydrogen phthalate, copper phthalate and copper tetraborate were described in the literature as dimeric and polymeric compounds. These substances have not yet been used as mediators so far.

Due to the addition of potassium hydrogen phthalate, sodium tetraborate or trisodium citrate, it was possible to markedly reduce the cross sensitivity to $H_2S$, surprisingly to completely eliminate the formation of elemental sulfur and, to markedly increase the sensitivity to $SO_2$ and to lower the residual currents.

An exemplary embodiment of the present invention is shown in the figure and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
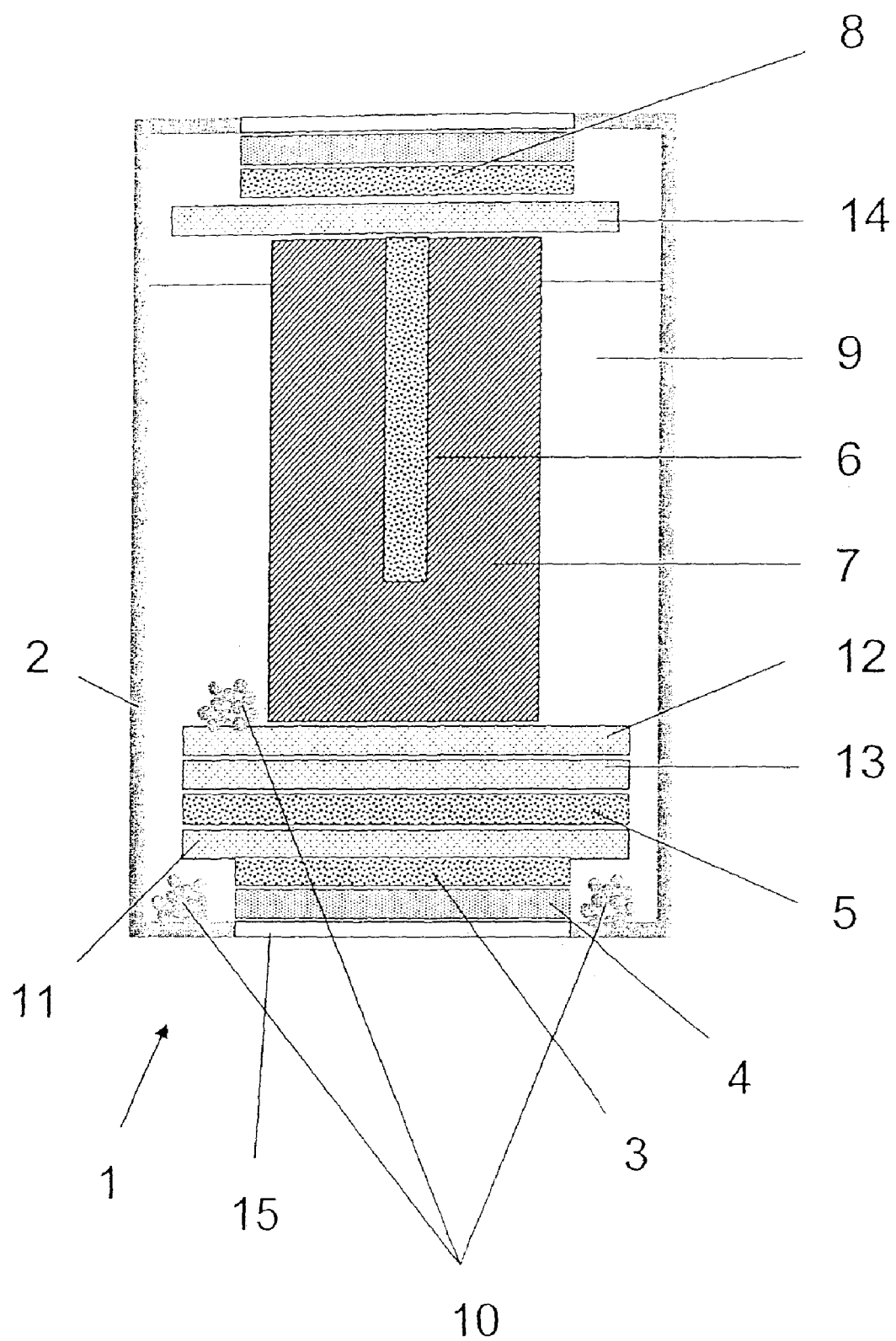
FIG. 1 is a longitudinal sectional view of a first electrochemical sensor.

Referring to the drawings in particular, in the first embodiment of a first electrochemical sensor 1, which is shown in FIG. 1, a measuring electrode 3 is arranged in a sensor housing 2 behind a diffusion membrane 4. A protective electrode 5, a reference electrode 6, a wick 7 and an auxiliary electrode 8 are also arranged in the sensor housing 2. The interior space of the sensor housing 2 is filled with an electrolyte-mediator mixture 9. The mediator is additionally also present as an excess solid 10. The measuring electrode 3, the protective electrode 5, the reference electrode 6 and the auxiliary electrode 8 are kept at fixed distances from one another by means of liquid-permeable nonwovens 11, 12, 13, 14.

The gas enters through an opening 15 in the sensor housing 2. The first electrochemical sensor 1 is connected to a potentiostat, which is not shown more specifically, in the known manner.

Figure 2:
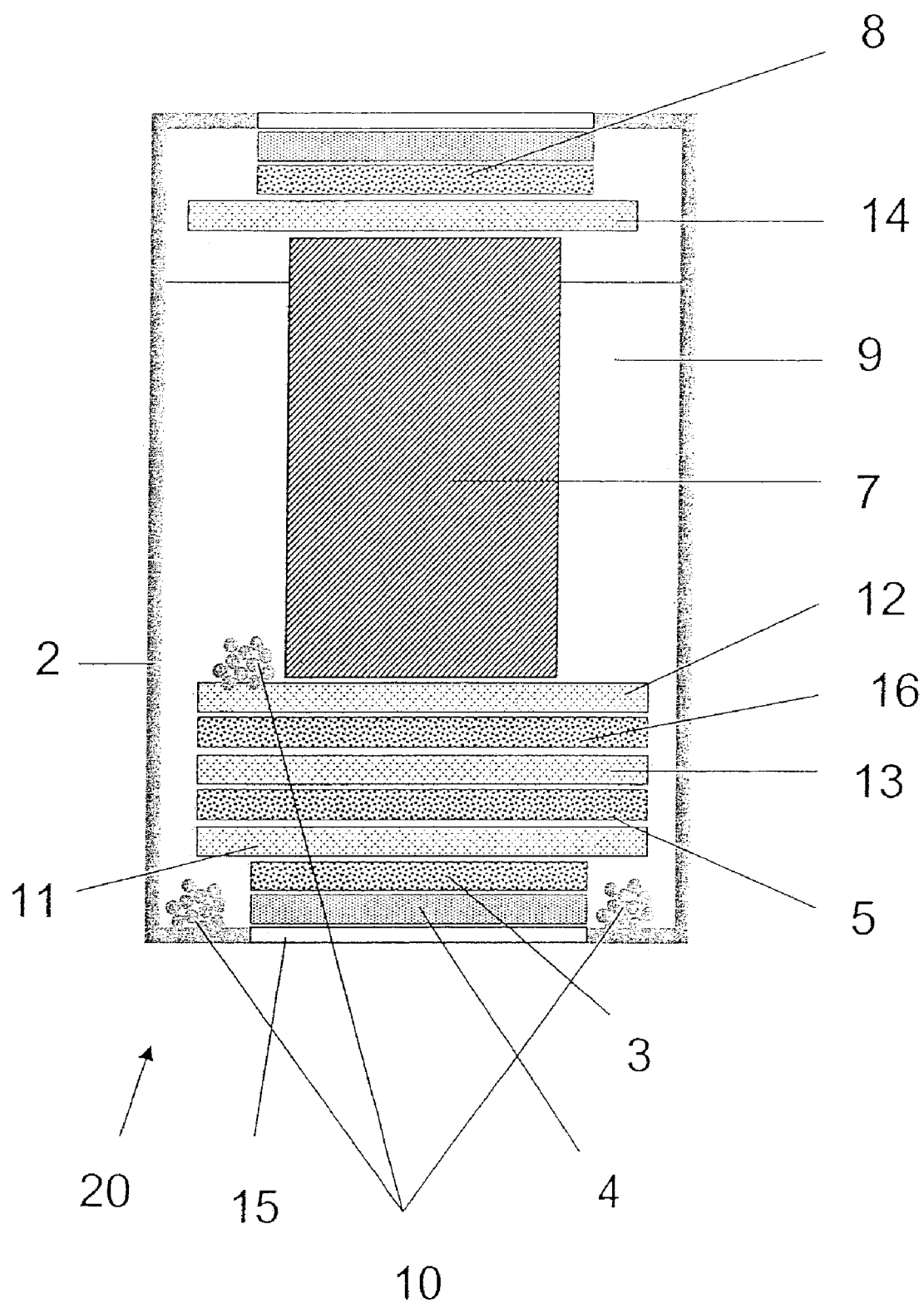
FIG. 2 is a longitudinal sectional view of a second electrochemical sensor.

FIG. 2 shows a second electrochemical sensor 20. Unlike in the first electrochemical sensor 1 according to FIG. 1, the second electrochemical sensor 20 does not have reference electrode 6 as shown in FIG. 1 and instead a disk-shaped reference electrode 16 is arranged behind the protective electrode 5. The second electrochemical sensor 20 otherwise has similar features. The interior space of the sensor housing 2 is filled with an electrolyte-mediator mixture 9. The mediator is additionally also present as an excess solid 10. Identical components are designated by the same reference numbers as in FIG. 1.

While specific embodiments of the invention have been shown and described in detail to illustrate the application of the principles of the invention, it will be understood that the invention may be embodied otherwise without departing from such principles.

What is claimed is:
1. An electrochemical gas sensor for detecting an analyte, the electrochemical gas sensor comprising:
   a housing defining an electrolyte space;
   a measuring electrode comprising a carbon-containing material, said measuring electrode being disposed in said electrolyte space;
   an auxiliary electrode disposed in said electrolyte space;
   a liquid electrolyte disposed in said electrolyte space; and
   an analyte-selective mediator, said analyte-selective mediator being provided in a saturated form in said electrolyte and being present as an excess solid in the electrolyte space, said measuring electrode detecting a concentration of one of $H_2S$ and $SO_2$ in a gas.
2. An electrochemical gas sensor in accordance with claim 1, wherein said measuring electrode comprises at least one of graphite, diamond-like carbon (DLC), carbon nanotubes (CNT) or boron-doped diamond (BDD).
3. An electrochemical gas sensor in accordance with claim 1, further comprising a reference electrode comprising at least one of graphite, diamond-like carbon (DLC) or boron-doped diamond (BDD) or carbon nanotubes.
4. An electrochemical gas sensor in accordance with claim 1, wherein said mediator comprises a mediator compound that is a transition metal salt of an acid compound, said acid compound containing at least two acid groups or at least one acid group and two hydroxyl groups.
5. An electrochemical gas sensor in accordance with claim 4, wherein said acid compound is a carboxylic acid.
6. An electrochemical gas sensor in accordance with claim 5, wherein said carboxylic acid is an aromatic carboxylic acid with two or three carboxyl groups, especially phthalic acid, isophthalic acid or terephthalic acid.
7. An electrochemical gas sensor in accordance with claim 4, wherein the acid compound is an aliphatic polycarboxylic acid, especially citric acid.

8. An electrochemical gas sensor in accordance with claim 4, wherein the acid compound is gluconic acid.

9. An electrochemical gas sensor in accordance with claim 4, wherein the acid compound is a boric acid.

10. An electrochemical gas sensor in accordance with claim 4, wherein said liquid electrolyte is a solution containing alkali or alkaline earth metal salts, preferably LiCl.

11. An electrochemical gas sensor in accordance with claim 4, wherein water or organic solvents including ethylene and/or propylene carbonate, are used as a solvent.

12. An electrochemical gas sensor in accordance with claim 4, wherein the transition metal salt is a copper salt or a $Cu^{2+}$ salt.

13. An electrochemical gas sensor in accordance with claim 12, wherein the Cu2+ salt is $CuCl_2$ and the concentration of $CuCl_2$ is between 0.2 mol and 1.0 mol in a 2-10-molar LiCl solution.

14. An electrochemical gas sensor in accordance with claim 12, wherein the Cu2+ salt is $CuCl_2$ and the concentration of $CuCl_2$ is about 0.5 mol in a 2-10-molar LiCl solution.

15. An electrochemical gas sensor in accordance with claim 4, wherein the transition metal salt is an iron salt or an $Fe^{3+}$ salt.

16. Electrochemical gas sensor in accordance with claim 1, further comprising a gas-permeable membrane, said housing having an opening with said gas-permeable membrane, wherein an analyte substance enters the area of said measuring electrode via said gas-permeable membrane.

17. An electrochemical gas sensor in accordance with claim 16, further comprising a reference electrode.

18. An electrochemical gas sensor in accordance with claim 1, further comprising a protective electrode arranged behind said measuring electrode.

19. A process of electrochemical gas sensing, the process comprising:
    providing a housing defining an electrolyte space;
    providing a measuring electrode comprising a carbon-containing material, said measuring electrode being disposed in said electrolyte space;
    providing an auxiliary electrode disposed in said electrolyte space;
    providing a liquid electrolyte disposed in said electrolyte space;
    providing an analyte-selective mediator;
    providing said analyte-selective mediator in a saturated form in said electrolyte;
    providing said analyte-selective mediator as an excess solid in the electrolyte space; and
    determining $SO_2$ concentration or $H_2S$ concentration in a gas using said measuring electrode.

20. A process of electrochemical gas sensing according to claim 19, wherein said electrolyte is or contains a chloride, wherein said analyte-selective mediator comprises one of potassium hydrogen phthalate, sodium tetraborate and trisodium citrate.

21. An electrochemical gas sensor in accordance with claim 1, wherein said analyte-selective mediator comprises one of potassium hydrogen phthalate, sodium tetraborate and trisodium citrate.

* * * * *